(12) United States Patent
Danto

(10) Patent No.: US 10,799,430 B2
(45) Date of Patent: Oct. 13, 2020

(54) POSITIVE PRESSURE FLOW SKIN ABRASION SYSTEM AND METHOD FOR DERMAL REJUVENATION

(71) Applicant: Allan Danto, Cardiff, CA (US)

(72) Inventor: Allan Danto, Cardiff, CA (US)

(73) Assignee: Med-Aesthetic Solutions, Inc., Cardiff, CA (US)

( * ) Notice: Subject to any disclaimer, the term of this patent is extended or adjusted under 35 U.S.C. 154(b) by 181 days.

(21) Appl. No.: 16/081,374

(22) PCT Filed: Jul. 24, 2017

(86) PCT No.: PCT/US2017/043546
§ 371 (c)(1),
(2) Date: Aug. 30, 2018

(87) PCT Pub. No.: WO2018/022517
PCT Pub. Date: Feb. 1, 2018

(65) Prior Publication Data
US 2019/0091113 A1      Mar. 28, 2019

Related U.S. Application Data

(60) Provisional application No. 62/494,005, filed on Jul. 25, 2016.

(51) Int. Cl.
*A61N 5/06* (2006.01)
*A61B 17/00* (2006.01)
(Continued)

(52) U.S. Cl.
CPC ........ *A61K 8/0204* (2013.01); *A61B 17/3203* (2013.01); *A61B 17/50* (2013.01); *A61B 17/545* (2013.01); *A61B 50/13* (2016.02); *A61K 8/19* (2013.01); *A61K 8/20* (2013.01); *A61K 8/26* (2013.01); *A61M 37/0092* (2013.01); *A61N 5/062* (2013.01); *A61N 5/0616* (2013.01); *A61N 5/0624* (2013.01); *A61Q 19/08* (2013.01); *A61B 2017/00747* (2013.01); *A61B 2017/00761* (2013.01); *A61B 2017/320004* (2013.01); *A61B 2017/32035* (2013.01);
(Continued)

(58) Field of Classification Search
CPC .............. A61B 17/3203; A61B 17/545; A61B 2017/00747; A61B 2017/00761; A61B 2017/00769; A61B 2017/320004
See application file for complete search history.

(56) References Cited

U.S. PATENT DOCUMENTS

| | | | |
|---|---|---|---|
| 6,375,635 B1 * | 4/2002 | Moutafis | A61B 17/3203 604/22 |
| 6,511,493 B1 * | 1/2003 | Moutafis | A61B 17/320758 606/167 |

(Continued)

*Primary Examiner* — Ryan J. Severson
(74) *Attorney, Agent, or Firm* — King & Partners, PLC

(57) ABSTRACT

The present invention is a dermal-exfoliation system that uses positive pressure to deliver salt and/or bio-inert crystalline particle abrasives or saline solution to the stratum corneum, combined with a minimal amount of negative pressure to close the loop when in contact with the skin to evacuate spent particles and dislodged skin cells and debris. An applicator handpiece is optimized for the use of the combined pressure system discussed herein for the removal of epidermal layers.

19 Claims, 8 Drawing Sheets

Figure 1:
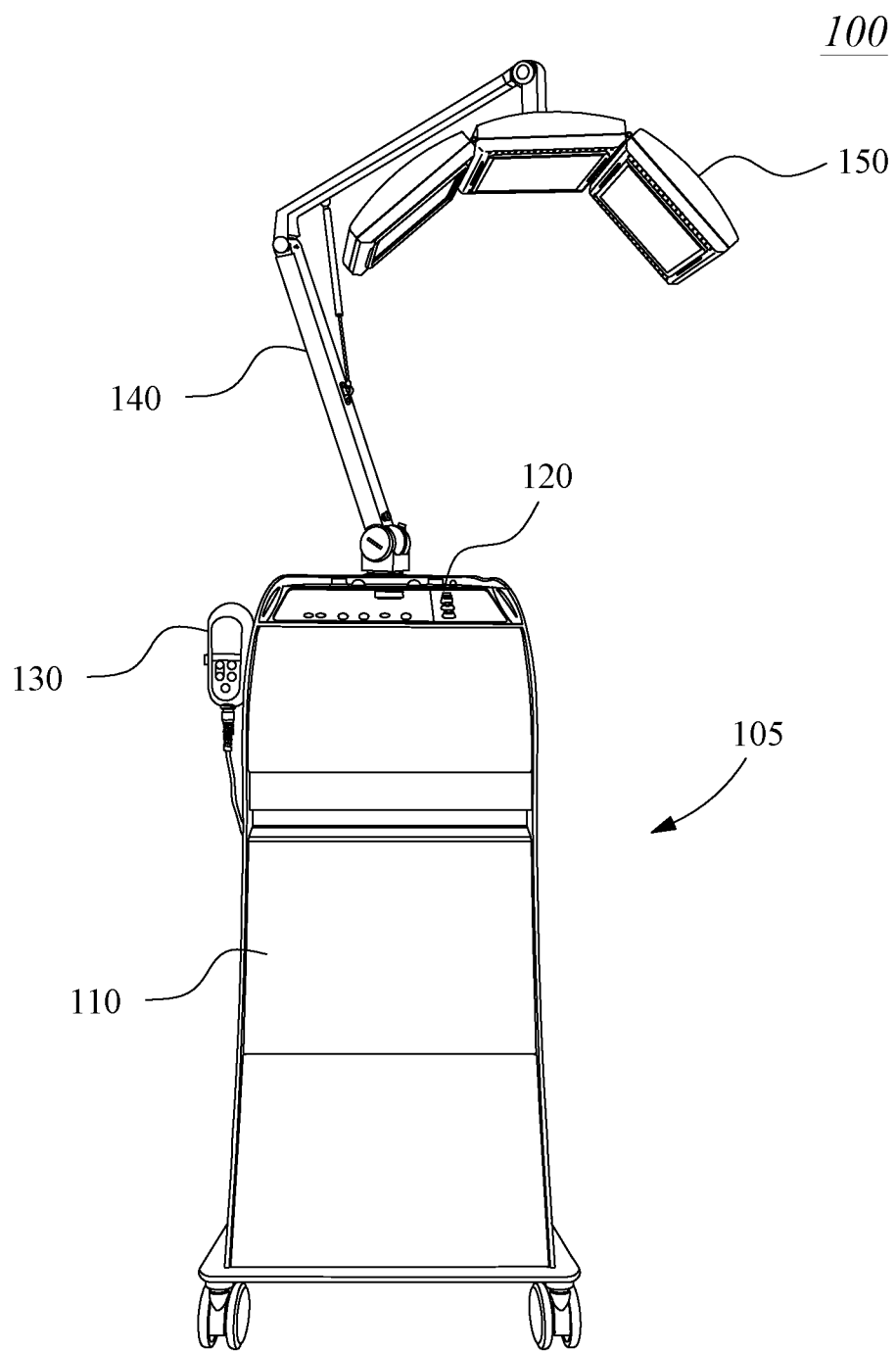

(51) Int. Cl.
*A61B 17/32* (2006.01)
*A61K 8/02* (2006.01)
*A61B 50/13* (2016.01)
*A61B 17/54* (2006.01)
*A61B 17/50* (2006.01)
*A61B 17/3203* (2006.01)
*A61K 8/19* (2006.01)
*A61K 8/20* (2006.01)
*A61K 8/26* (2006.01)
*A61M 37/00* (2006.01)
*A61Q 19/08* (2006.01)

(52) U.S. Cl.
CPC ... *A61B 2217/005* (2013.01); *A61B 2218/007* (2013.01); *A61K 2800/28* (2013.01); *A61K 2800/87* (2013.01); *A61M 2037/0007* (2013.01); *A61N 2005/0652* (2013.01); *A61N 2005/0659* (2013.01); *A61N 2005/0663* (2013.01)

(56) References Cited

U.S. PATENT DOCUMENTS

| | | | |
|---|---|---|---|
| 6,562,050 B1 | 5/2003 | Owen | |
| 6,615,014 B2* | 9/2003 | Sugihara | G03G 15/0822 399/254 |
| 6,726,693 B2* | 4/2004 | Weber | A61M 35/00 451/75 |
| 6,764,493 B1 | 7/2004 | Weber et al. | |
| 8,518,031 B2* | 8/2013 | Boyden | A61K 9/0019 606/22 |
| 8,814,836 B2* | 8/2014 | Ignon | A61M 35/003 604/289 |
| 9,308,024 B2* | 4/2016 | Whyte | A61B 17/3203 |
| 9,642,997 B2* | 5/2017 | Ignon | A61B 17/32 |
| 9,649,131 B2* | 5/2017 | Beijens | A61B 17/54 |
| 10,172,644 B2* | 1/2019 | Ignon | A61B 17/545 |
| 10,556,097 B2* | 2/2020 | Ignon | A61B 17/32 |
| 2001/0023351 A1 | 9/2001 | Eilers et al. | |
| 2001/0021324 A1 | 10/2001 | Bernabei et al. | |
| 2002/0058952 A1* | 5/2002 | Weber | A61M 35/00 606/131 |
| 2004/0092920 A1* | 5/2004 | Rozenshpeer | A61B 18/02 606/22 |
| 2004/0219179 A1* | 11/2004 | McDaniel | A61K 8/678 424/401 |
| 2006/0229550 A1* | 10/2006 | Staid | A61B 17/3203 604/27 |
| 2010/0152880 A1 | 6/2010 | Boyden et al. | |
| 2010/0228273 A1* | 9/2010 | Staid | A61B 17/3203 606/167 |
| 2010/0298760 A1* | 11/2010 | Olle | A61M 37/0015 604/20 |
| 2011/0224691 A1 | 9/2011 | Whyte et al. | |
| 2016/0008031 A1 | 1/2016 | Beijens et al. | |
| 2016/0038183 A1* | 2/2016 | Ignon | A61M 35/003 606/3 |
| 2019/0091113 A1* | 3/2019 | Danto | A61K 8/20 |

* cited by examiner

POSITIVE PRESSURE FLOW SKIN ABRASION SYSTEM AND METHOD FOR DERMAL REJUVENATION

CROSS-REFERENCE TO RELATED APPLICATION(S)

This application claims the benefit of and is a National Stage entry of PCT Application No. PCT/US2017/043546 filed Jul. 24, 2017, which claims the benefit of U.S. Provisional Patent Application No. 62/494,005, filed Jul. 25, 2016, the contents of which are hereby incorporated by reference in its entirety.

FIELD

The invention relates in general to the field of skin treatment, and more specifically to improved systems for performing dermabrasion, microdermabrasion, skin resurfacing and skin exfoliation techniques on human skin to aesthetically, cosmetically and therapeutically cause improvement thereto.

BACKGROUND

Human skin is comprised of the dermis (deep) and epidermis (superficial). The epidermis is further comprised of multiple layers that include the stratum corneum (outermost), the stratum lucidum, stratum granulosum, stratum spinosum, and stratum basale. Removal of portions of these layers is interpreted by the body as mild injury and results in a healing response to replace lost skin cells.

Dermal-exfoliation techniques can be generally divided into three categories depending upon the depth of skin removal. The most superficial exfoliation or peel extends into the epidermis. A more aggressive, medium-depth resurfacing treatment, extends into the papillary dermis, and deep resurfacing treatments remove tissue to the depth of the reticular dermis. Dermal-exfoliation-induced damage to the skin induces an inflammatory stage and subsequent healing response. As dermal and epidermal skin cells are replaced, a new outer layer of skin is formed, and stimulation of a renewed extracellular matrix is achieved as fibroblasts synthesize the formation of new layers of collagen. The new layer of skin so formed more closely resembles the physiology and appearance of younger and more normal skin. Skin abrasion by these techniques has been used as a treatment to smooth scars, blemishes, or to treat other skin conditions that may be caused by, for example, acne, acne scars, sun exposure, rhytides, hyperpigmentation, solar elastosis, other dyschromias, stria distensae, seborrheic dermatitis, stretch marks, etc.

As is well known, various approaches for dermal exfoliation is practiced in the cosmetic field, ranging from laser ablation, chemical peels, needle traumatization, fruit pit exfoliation crèmes and so forth. Each of these approaches has their benefits and issues, the field being very competitive for schemes with better efficacy. Accordingly, a new and improved approach utilizing positive pressure flow with salts (for example, as the abrasive media) with a specialized delivery apparatus is described below.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosed embodiments, a positive pressure skin exfoliating system is provided, comprising: a positive air pressure source; a dehumidifier, dehumidifying both air from the air pressure source and air in a chamber configured to contain a skin exfoliating abrasive container; a plurality of dehumidifying stages coupled to the dehumidifier; at least one of a controller and a regulator for controlling a pressure value of pressurized air from the air pressure source; an input tube with the pressurized and dehumidified air, coupled to the skin exfoliating abrasive container; an output tube for collecting waste from a skin treatment site; a vacuum eductor coupled to the output tube; and an exfoliating handpiece with an angle of impingement with respect to a subject tissue comprising: a hose-end on one side and a skin treatment end on the other side, the hose-end being coupled to the input tube and the output tube; a deflection chamber at the skin treatment end; a skin interface at a bottom of the deflection chamber; and input and output channels traversing an interior of the handpiece from the hose-end to the interior deflection chamber end, the input channel being under a positive pressure from the air pressure source and channeling an abrasive to the skin interface, and the output channel being under a vacuum pressure and channeling used abrasive and dermal waste from the deflection chamber.

In another aspect of the disclosed embodiments, the above system is provide, wherein the chamber is a sealable chassis; and/or wherein the sealable chassis also houses the pressure source, filtering stages, and skin exfoliating abrasive container; and/or the container contains a skin exfoliating abrasive that is a salt composed from sodium chloride; and/or wherein the container contains a skin exfoliating abrasive is aluminum oxide or sodium bicarbonate; and/or further comprising a waste container connected to at least one of the vacuum educator and dehumidifying stages; and/or wherein the angle of impingement of the handpiece is at least one of approximately between 20°-50°, 15°-45°, 22°-27°, and approximately 25°; and/or further comprising an ultrasonic transducer for treatment of exfoliated skin; and/or wherein the ultrasonic transducer operates at a frequency of one of 1 MHz, 2 MHz, 3 MHz, 3.3 MHz, or 5 MHz; and/or further comprising an adjustable lamp that emits light within a range of 400 nm to 2940 nm; and/or wherein the pressurized air is controlled to a maximum of approximately 60 PSI and is provided to ensure the positive pressure is managed and adjusted to a level of between 24-45 PSI; and/or wherein the deflection chamber is approximately 13 mm in longitudinal length, and approximately 7 mm in depth; and/or wherein the deflection chamber is approximately between 13-16 mm wide and approximately 14 mm tall.

In yet another aspect of the disclosed embodiments, a method for dermal exfoliation for skin rejuvenation is provided, comprising: pressuring air; dehumidifying the air; and directing an abrasive under positive pressure onto tissue through an angled handpiece, having an angle of impingement of approximately between 20°-50°, or 15°-45°, or 22°-25°, or approximately 25° and having: a hose-end on one side and a skin treatment end on the other side, the hose-end being coupled to an input tube and an output tube; a deflection chamber at the skin treatment end; a skin interface at a bottom of the deflection chamber; and input and output channels traversing an interior of the handpiece from the hose-end to the interior deflection chamber end, the input channel being under a positive pressure from a air pressure source and channeling the abrasive to the skin interface of the handpiece, and the output channel being under a vacuum pressure and channeling used abrasive and dermal waste from the deflection chamber; wherein at least one of a reduction of sun-damage, weather damage and age spots, reduction of irregular pigment patterns in healed scars, smoothing of fine lines, wrinkles and acne pitting, improvement of skin strength, elasticity/smoothness, and appearance of stretch marks is obtained.

In another aspect of the disclosed embodiments, the method above is provided, further comprising at least one of applying an ultrasonic signal with a frequency of one of 1 MHz, 2 MHz, 3 MHz, 3.3 MHz, or 5 MHz and a light within a range of 400 nm to 2940 nm to a treated area.

DETAILED DESCRIPTION

Introduction

The removal of the uppermost layers of the stratum corneum via microdermabrasion techniques can be performed by particle abrasion or non-particle abrasion means. Particle-based microdermabrasion involves accelerating crystalline particle abrasives along a closed loop vacuum circuit interposed by a roughly linear handheld apparatus (i.e. a handpiece) that opens to the skin to provide a focal point for skin abrasion. Motive force for the flow of crystalline particle abrasives is typically provided by an apparatus that utilizes negative pressure applied at one end of the circuit to create suction pressure at the other end of the circuit. Flexible tubing is employed that is capable of withstanding pressure sufficient to deliver the crystalline particle abrasives onto the skin and thereafter remove the spent particles and cellular debris from the site of application to the skin without collapsing or kinking the tubing.

Typical prior-art particle-based dermabrasion/microdermabrasion apparatus use a vacuum circuit that includes at least i) flexible input tubing to provide unidirectional flow of crystalline abrasive particles from a particle storage repository joined to one end of a ii) user-controlled handpiece, which comprises internal parallel input and output channels that are open to each other only at the skin-contacting surface of the handpiece to thereby provide for the controlled delivery of the accelerated crystalline abrasive onto the skin, and iii) flexible output tubing, which carries spent particles and cellular debris to a waste container. Contact of the skin-contacting window of the handpiece with the skin closes and seals the vacuum circuit. Application of negative pressure to one end of the circuit thus pulls skin into the skin contacting window of the handpiece, and also provides for the abrasive particle flow that bombards the epidermis and subsequently removes the resulting particle and cellular waste material from the site of skin contact.

However, such prior art systems introduce the prolonged application of negative pressure to the skin, which, more often than not, can cause a variety of side effects and problems. For example, studies indicate that the skin typically cannot tolerate prolonged suction/vacuum exceeding 22 mm hg, and that exceeding this limit for a period of time can result in vacuum-induced bruising, erythema and edema as a result of this type of aggressive microdermabrasion. This is especially true for certain skin types, such as skin that is particularly thin, of color (Fitzpatrick scale III through VI), is sensitive to pulling, tugging or tearing, or bruising/edema induced discoloration. Furthermore, applying a constant vacuum level to different regions of the skin having different thickness and elasticity may result in an unpredictable range of effects given the degree of suction-induced stretching experienced by the skin. For example, acute trauma is more likely in regions where the skin is very thin such as the eyelid, while conversely insufficient trauma may be experienced by thicker skin, such as that on the back.

Thus, in view of the shortcomings of the prior art, there has been a long-standing need for a dermal-exfoliation system that reduces or eliminates the exposure of skin to the prolonged high vacuum pressures typically employed during treatments of the prior art. Such a system would reduce the trauma to structures underlying the epidermis such as blood vessels and extracellular compartments induced by prolonged exposure to negative pressure, and would increase the pool of patients for whom current therapies are presently unusable given the presence of contraindications such as particularly thin skin, of color (Fitzpatrick scale III through VI), as well as skin that is sensitive to pulling, tearing, bruising or discoloration.

Concomitant to the need to reduce or eliminate the prolonged vacuum effects, it is known that a variety of crystalline particle abrasives have been used to accomplish dermal abrasion, with a preference in the prior art for the use of aluminum-based crystals, including aluminum oxide. The use of sodium chloride has been attempted given its compatibility with human skin and non-toxic nature when applied externally, but its use has fallen by the side since the microscopic structure of the typical salt crystal used is very irregular and fragile, and has not been able to provide the consistency necessary for the level of skin abrasion necessary for cosmetic and/or therapeutic efficacy. In contrast, aluminum oxide is able to maintain its crystalline structure and abrasive capabilities as it is propelled onto the skin, but the presence of aluminum has been implicated in a variety of complications experienced by the human body, ranging from the clogging of skin pores to some evidence suggesting that in women it was found in greater quantities in the brains of those who have suffered from Alzheimer's disease.

Correspondingly, there has also been a long standing need in the art for the design of an apparatus capable of performing dermal-exfoliation by utilizing sodium chloride, for example, as the abrasive media in a manner that allows for the sodium chloride to retain its crystalline abrasive property as it contacts the skin.

DESCRIPTION

In view of the above, an improved design of the mechanism of providing for the flow of such particles, and/or an improved design of the handpiece is provided that allows the operator to optimize control of the particle stream as it relates, for example, to the angle of contact between the handpiece and the skin to be treated.

Therefore, one or more of the exemplary embodiments described here relate to an apparatus for treating skin for dermabrasion, microdermabrasion, or skin exfoliation, using a handheld assembly (e.g. a handpiece) specially configured to deliver a stream of crystalline abrasive particles from the housing to the surface of the skin optionally under positive pressure, and further to collect the delivered (waste) crystalline abrasive particles, dislodged skin cells and/or skin debris back to the housing. The one or more various embodiments comprise means of providing positive pressure and optionally negative pressure from the central control unit to the handpiece. A user input device allows for control of the amount of pressure applied. The handheld assembly is connected to the housing (which includes a dehumidification device that keeps the housing at humidity levels below 50%) where by a hose or hoses that provide a means of passaging cargo such as abrasive salts and/or crystals and/or skin debris to an input and/or output repository.

The handpiece can also be used to direct air flow containing tiny crystals of a desired media, for example, aluminum oxide, sodium chloride, or sodium bicarbonate, etc. The one or more embodiments relate to the function and structure of the positive pressure system for providing propulsion to the crystalline particle abrasive along the input channel and through the handpiece to accelerate a particle current on to the skin. An output channel capable of providing negative pressure from the skin-contacting portion of the handpiece can be used in order to remove cellular, and or crystalline particle abrasive debris from the site of skin contact.

FIG. 1 is an illustration 100 of an exemplary dermal-exfoliation system 105, showing the outer chassis 110, control panel 120, remote ultrasound transducer/controller 130, articulating arm 140 coupled to adjustable lamp 150. Obscured from view is the exemplary handpiece. Interior to chassis 110 are the various positive pressure system(s), abrasive containers/filter, temperature/moisture controller systems. The embodiment of FIG. 1 demonstrates a very compact and functional unit as well as one that is mobile, having rollers/casters on the bottom of the outer chassis 110.

Figure 2:
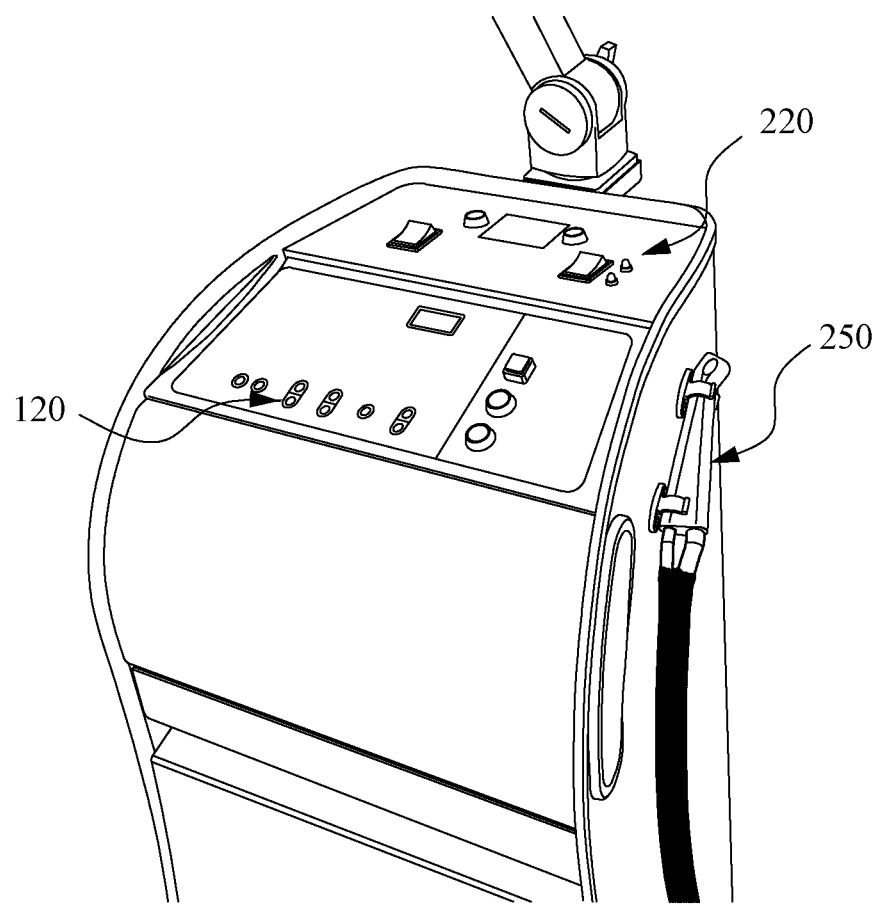

FIG. 2 is an illustration 200 of an embodiment of control panel(s) 120 for an exemplary system, with associated power & crystalline control switches 220, and exemplary handpiece 355250. The control panel 120/crystalline control switches 220 contain multiple "buttons" or switches and indicators for controlling operation of the system 105 of FIG. 1, and are understood to be well known in the art. For example, buttons/switches/gauges/lights to control and provide the status of the various sub-systems in the system 105, such as the vacuum, abrasive level, flow rate, pressure, heat, filter status, waste status, lights, and so forth are situated on the control panel(s) 120/220 as shown or can be distributed on other sides/faces of the system 105, as according to design preference.

Figure 3:
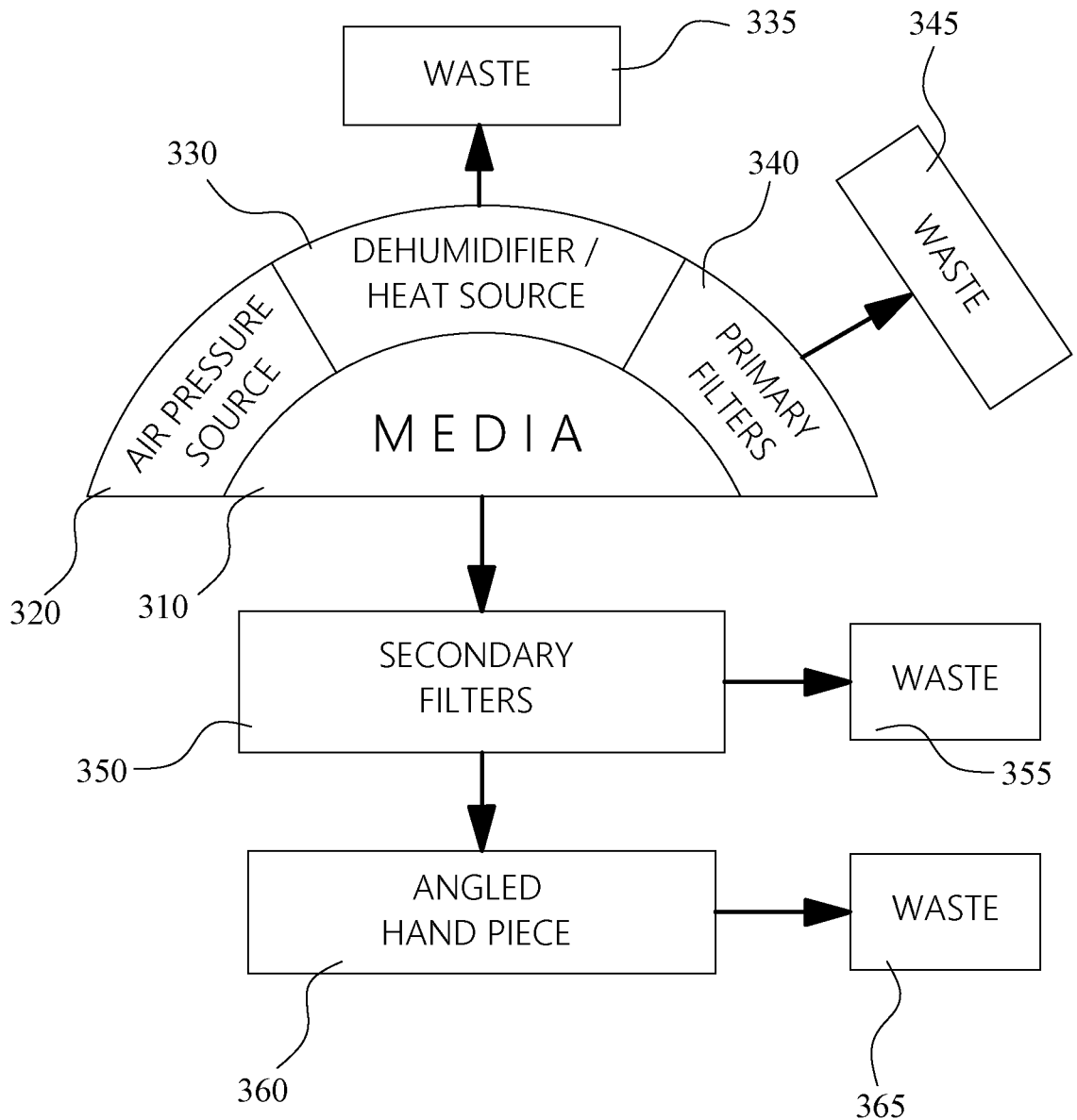

FIG. 3 is a block diagram 300 illustrating the top-level subsystems and their interaction with the media and each other. For the purposes of ease of explanation only, the media will be referred to as "salt" in the various embodiments, understanding that other abrasive type media may be used, if so desired. Media (or salt) 310 is operated on by a combination of air pressure source 320, dehumidifier/heat source 330 and primary filters 340, either sequentially or in concert.

In one embodiment, positive air pressure source 320 is dehumidified 330 and transports salt 310 from its reservoir, whereupon the dehumidified salt is filtered through one or more primary filters 340 to result in a "$1^{st}$ stage filtered and dehumidified" abrasive. The extracted moisture (or water) from the dehumidifier 330 is evacuated as waste 335, either as vented moisture or through a waste tank (not shown) or drain (not shown), as is the waste-filtered salt 345 and/or 365. In some embodiments, the dehumidifier may be a moisture absorbent solid that is controlled to provide the desired moisture level in the salt (for example, through one of the switches/controls shown in FIG. 2). It should be appreciated that the primary filters 340 may comprise one filter, or a series of multiple filters that operate to select the appropriate size and "quality" of salt for $1^{st}$ stage filtering. The $1^{st}$ stage filtered and dehumidified salt is then processed by secondary filters 350, if an additional level of filtering for higher "quality" salt is desired. The $2^{nd}$ stage filtered and dehumidified salt's waste products are similarly extracted as waste 355 and/or 365. The ensuing salt is then of the appropriate size and quality and humidity to effect appropriate usage as a superior dermatological abrasive and forwarded via air pressure source 320 (or a secondary air pressure system, if so desired) to the angled handpiece 360. Exfoliates and the expended salt is thereafter collected in the waste receptacle 365 from the angled handpiece 360.

It should be noted that in some embodiments, the various wastes (345, 355, 365) may be channeled to a single "waste" container, if so desired. Also, while the dehumidifier 330 is shown as only affecting the $1^{st}$ stage process, it is understood that in some embodiments, the dehumidification will also be applied to the $2^{nd}$ stage process, thus ensuring that the salt is not re-humidified by ambient air once exiting the $1^{st}$ stage process. Therefore, in these latter embodiments, the "dehumidification" will comprise a closed system, for example, the entirety of the interior of the chassis 110 as shown in FIG. 1 may be a sealed enclosure or partially sealed with respect to the subsystems that require dehumidification.

Figure 4:
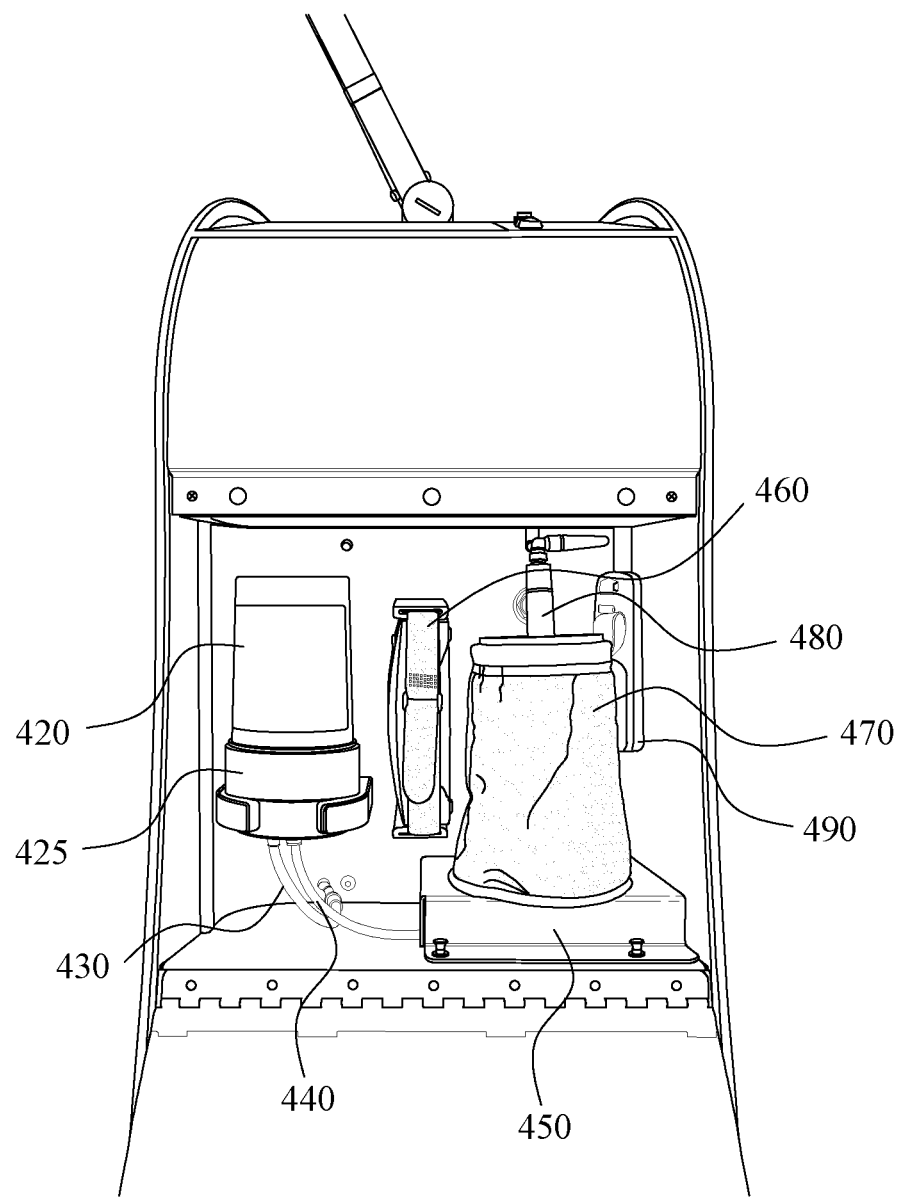

FIG. 4 is an interior view 400 of the Humidity Controlled Salt Chamber, and major subsystems within chassis 110. Salt canister 420 contains the abrasive media, which may be a disposable container and/or one pre-filled supplied by the supplier. At the bottom of the salt canister 420 is a positive pressure infusion cap (PPIC) 425, interfaces with the salt canister 420 to provide salt to the powder feed system 450 (the cover of the powder feed system being shown in the FIG.). At the bottom of the PPIC 425 are a pair of tubes 430 and 440, tube 430 providing clean dry air pressure into the salt canister 420, and tube 440 providing a pathway for the salt from the PPIC to the powder feed system 450. Dehumidifier 460 provides the appropriate humidity (which is typically, but not necessarily, under 50%). Waste heap-filter bag 470 collects the used salt and skin debris and is typically disposable. A particle recovery system or Eductor 480 is atop of waster filter bag 470 and operates to recover excess particles from the treatment site while maintaining the positive pressure induced velocity. To monitor the humidity, humidity sensor 490 tracks the humidity and relays via a direct connection or wireless, to the user, the humidity status. The humidity sensor 490, in some embodiments, can be removed from the chassis 110 and placed in a room to see if the room's humidity is adequate.

Figure 5:
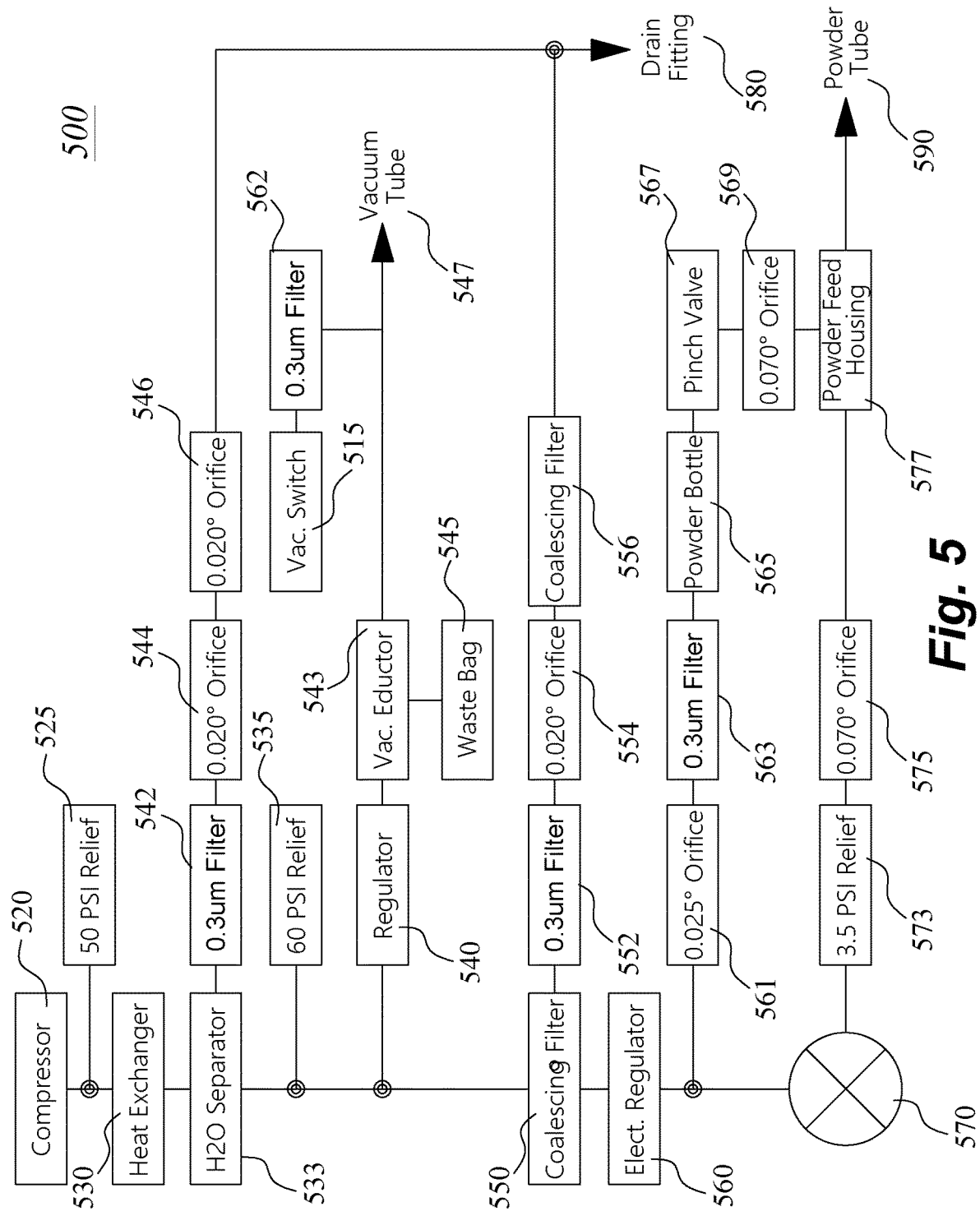

FIG. 5 is a block diagram 500 illustrating the various functional blocks in one or more of the described embodiments. It should be understood that some of these elements are optional. For completeness, block diagram 500 is illustrated with all optional components listed.

Air compressor 520 provides the system and salt movement air pressure with relief valve 525 (shown here as being set at, for example, approximately 50 pounds per square inch (PSI)), which provide a single stage step down pressure adjustment. Heat exchanger 530 and dehumidifier ($H_2O$ Separator) 533 are in line with the compressor 520, operating to cool and dehumidify the pressurized air as well as for the salt being moved. The heat exchanger 530 can be a coil based system capable of dehumidifying down to 35% relative humidity. The dehumidifier 533 can provide multiple functions, such as providing variable pressure to the powder bottle (565) and overall pressure to the vacuum eductor (543), as well as pressure to evacuate moisture. A series of first stage air filters 542, 544, and 546 provide various finer degrees of filtering air to move the salt. For example, filter 542 provides 0.3 um size filtering for removing water vapor from heat exchanger 530. A series of two one-way filters 544 and 546 provides 0.020" filtering and prevent back-flow. Any water/waste (moisture) from the various filters is channeled to drain or waste collector 580. A secondary adjustable relief valve 535 with a maximum of approximately 60 PSI is provided to ensure the positive pressure is managed and adjusted to a level of between 24-45 PSI.

Pressure regulator 540 is also connected to the compressor stream with vacuum eductor 543, which directs the waste to waste bag 545. The pressure regulator 540 provides a pressure "step-down" to better pull the used salt and waste to the waste bag 545. Additionally, this pressure is also sent to the handpiece vacuum tube for 547 for transport of used material. Vacuum eductor 543 is also connected to vacuum tube 547, which is in turn coupled to a vacuum switch 515 and 0.3 um filter 562. Next, secondary filters 0.3 um 552, 0.020" 554, and 0.020" 556 are used in combination with coalescing filter 550. Coalescing filter 550 operates as the beginning of the second stage filtering, which is similar to the first stage filtering. An electronic regulator 560 is downstream from the coalescing filter 550. The regulator 560 controls the voltage and the pressure settings set at the user interface/control panel. Thus, regulated, stepped down, adjustable and variable PSI positive pressure from the regulator 560 is sent through a 0.025" orifice 561, which is followed by an additional filtering level comprised of a 0.3 um filter 563 which leads to powder bottle 565. This moisture filtered, adjustable pressured air creates the positive pressure in the powder bottle 565, to push the abrasive in the powder bottle 565 to the pinch valve 567.

Pinch valve 567 is connected to the powder bottle 565 and is then connected to the powder feed housing 577 through the 0.070" orifice 569. The pinch valve 567 is set to be in a closed state until the loop of pressure is "closed" at the handpiece when in contact with the skin. When contacted, the pinch valve 567 is opened and abrasive material is fed through the 0.070" orifice 569. Powder feed housing 577 mixes dehumidified positive pressure and filtered air and distributes the filtered and dehumidified salt at the intensity set on the control panel 120. Pressure distributor 570 is downstream from electrical regulator 560 and is coupled to a 3.5 PSI relief 573, and connected to a tubing through the 0.070" orifice 575 and to the subsequent powder feed housing 577. The pressure distributor 570 distributes the adjusted pressure to propel the abrasive material into the handpiece. The air velocity is optimized by passing through the 0.070" orifice 575 where it mixes with the abrasive material from the powder feed housing 577. The powder feed housing 577 is connected to the powder tube 590 that leads to the handpiece.

Figure 6:
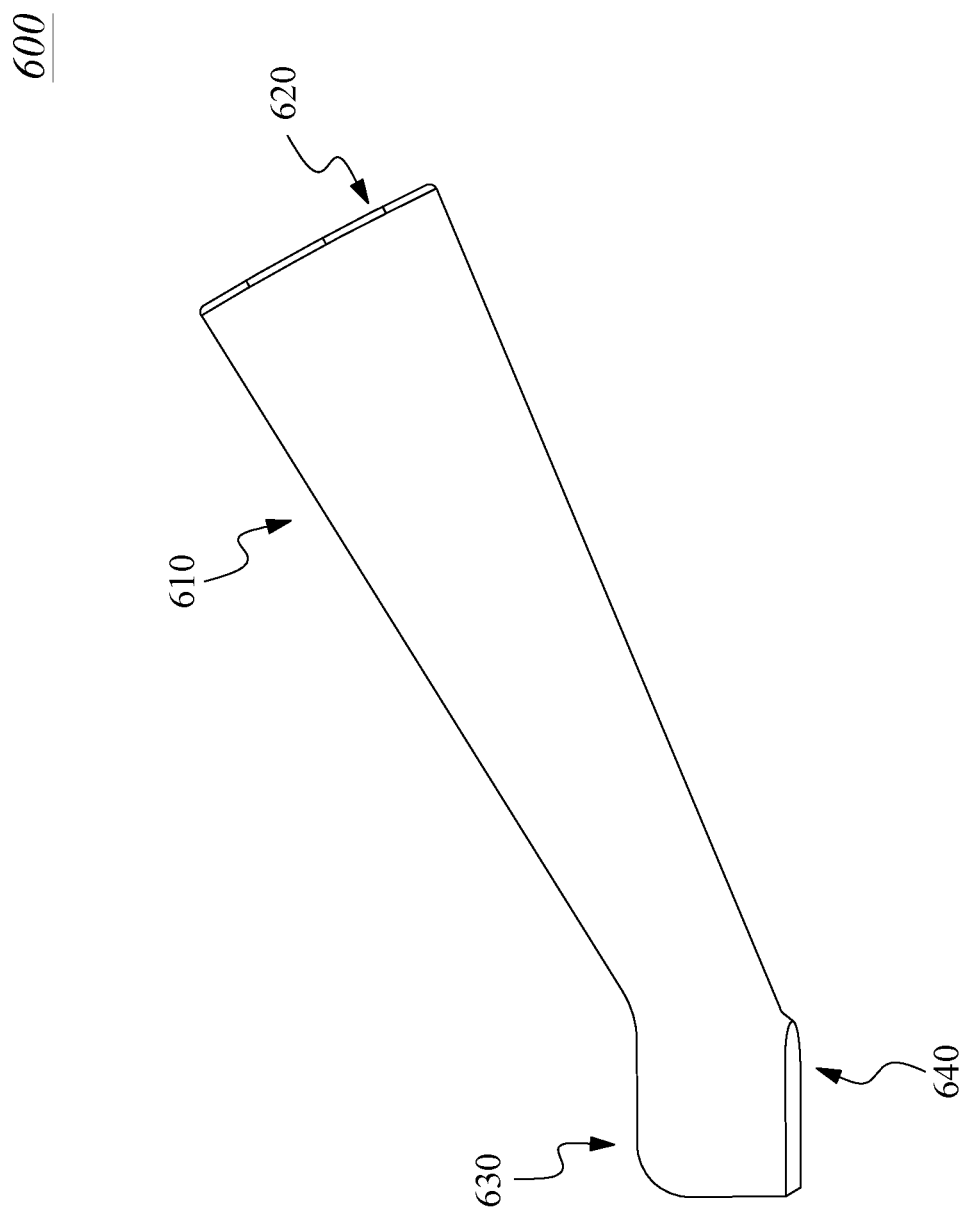

FIG. 6 is a side view illustration 600 of the exemplary handpiece assembly 610, which is generally a longitudinal solid structure with an opening at the surface side 640 and with tube ends at the opposite end of the longitudinal axis or the 620 side. The handpiece has a skin-contacting surface 640 at the head 630 of its longitudinal axis, and an "exchange" surface 620 at the opposite end of its longitudinal axis. The "exchange" (i.e. non-skin contacting) end 620 of the handheld assembly's longitudinal axis may be configured with fittings that enable the attachment of input or output hoses, or preferably both, wherein said input and/or output hoses connect to the central control unit which may optionally have repositories for providing the crystalline abrasive particle to the input channel and/or waste receptacles for receiving matter from the output channel. Such connections may comprise vacuum tubing, or surgical tubing, or any other known connective material that is capable of withstanding pressure provided by the apparatus and that is capable of both transmitting crystalline abrasive to the skin and removing waste material away from the site of skin contact.

The handpiece assembly 610 may be designed so that its longitudinal axis with respect to the skin-contacting surface 640 constitutes an "angle of impingement." The "angle of impingement" or the angle at which the abrasive medium impacts the tissue has a direct correlation to the patient's discomfort level. The greater the angle of impingement, the greater the degree of discomfort. Thus, in one embodiment, the handpiece assembly 610 may be designed to have an angle of impingement wherein the plane of the skin-contacting surface relative to the axis of the handheld assembly 610 is at an angle less than 90°, specifically between 20°-50°. In most embodiments, the angle will be between 15°-45° and an optimal angle range is somewhere in the range of 22°-25°. In a prototype embodiment, the angle was set to 25° with superior results. Use of these lesser angles results in less discomfort and a more aggressive, efficient procedure.

Figure 7:
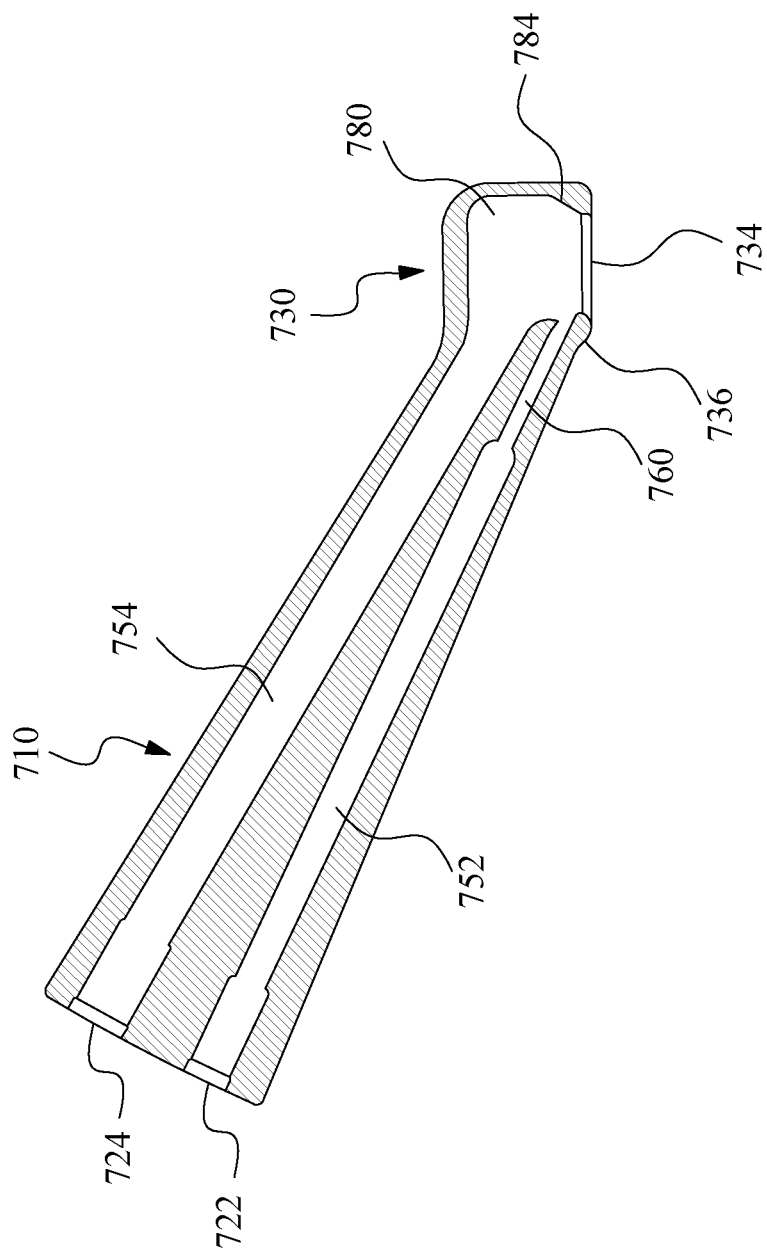

FIG. 7 is a cut-away illustration 700 of the exemplary handpiece assembly showing coupling ports 722 and 724 at the exchange side. The coupling ports 722, 724 allow for easy insertion of the respective tubes (not shown). The coupling ports 722, 724 communicate with the head 730 of the handpiece assembly via two channels, input channel 752 and output channel 754 that travel throughout the length of the handpiece assembly to skin-contacting interface 734. The channels 752, 754 can be cylindrical channels, with uniform cross sections or with non-uniform cross sections, depending on design preference. In the embodiment shown in FIG. 7, the channels are of uniform cross section with the exception of input channel uniform 752 with has a secondary smaller channel 760 at it approaches the skin-contacting interface 734. Head 730 contains the deflection chamber 780, the chamber openings for the input, output channels (752, 754), and the skin-contacting interface 734. Deflection chamber 780 is sized both in length and height to be larger than the combined sizes of the input/output channels to allow abrasives/salts, cell and skin particulates to deflect off of the deflection wall 784 and be "sucked" into the output channel 754. It should be understood that the term "deflection" with respect to the deflection chamber 780, is a general term. That is, if the chamber is sufficiently long or the applied pressure is sufficiently low, there will be no so-called deflection of exfoliated tissue or abrasive occurring in the chamber, but simply redirected to the output channel 754. Therefore, the term "deflection chamber" is understood to encompass both deflection occurrences as well as non-deflection occurrences within the deflection chamber 780.

In a prototype embodiment, the deflection chamber 780 was configured to be approximately 13 mm in longitudinal length, with a depth of approximately 7 mm. The height of the deflection chamber 780 was approximately between 13-16 mm and approximately 14 mm tall. The angle of impingement was approximately 25 degrees. Of course, these values are simply representative of a prototype and therefore other sizes, dimensions and so forth may be used without departing from the spirit and scope of this disclosure.

The input channel 752 is situated below the output channel 754 and targeted to a "rear" portion of the skin-contacting interface 734, with separation allowance from the deflection wall 784 to minimize "wall" ricochet effects from the impinging salt. At one side of the terminal end of the skin-contacting interface 734, a bulbous or curved surface 736 is provided to make it easier for the head 730 to be tilted without causing the "unsealing" of the skin-contacting interface 734 from the skin and/or allowing the head 730 to be moved across the patient's skin without causing "edge" discomfort.

In operation, when the handpiece is in contact with the skin, pressure is applied to the output channel 754 by means of a suction mechanism to create a vacuum that causes crystalline particle abrasives to be aspirated from a humidity controlled storage repository into the input channel 752. Thus, crystalline particle abrasives are propelled through the input channel 752 of the handpiece, which directs the flow of tiny particulate crystalline abrasives onto the skin at high speed, which abrades the skin and wears away cell layers with each pass of the handpiece. At the skin-contacting interface 734 of the handpiece, the crystalline abrasives are aspirated propelled through the input channel 752 and dislodged skin cells and debris from the skin surface are removed from the site of contact through the output channel 754 of the handpiece.

The mechanism by which force and momentum are conferred to the abrasive particles occurs by means of generating a positive pressure loop at the one end of the input channel 752 onto the skin, and back out through the output channel 754 through a vacuum loop. Accordingly, both a positive pressure and negative pressure system is utilized. Specifically, positive pressure applied to one end of the loop provides abrasive particles to the skin-contacting interface 734 of the handpiece when in contact with the skin and is evacuated by negative pressure in the output channel 754. A balance of pressures is required and is accomplished as a closed system which and requires contact with the skin to form the closed system.

It should be appreciated that contact with the skin can be amplified through one or more orifices (not shown) on the handpiece, to thereby engage the skin, and further to create the force which draws the particles from an input orifice on the handpiece, and thereafter away from the skin and into the waste repository. It should further be appreciated that the closed loop may be a semi-closed loop system, wherein a complete seal is not necessary since even with reduced pressure, there is sufficient force to provide adequate operation.

The handpiece of the inventive apparatus has thus been designed to deliver crystalline abrasives via a pressure cycle in a semi-closed loop system. The handpiece is contacted with the surface of the skin to provide abrasive particles from a storage repository and thus direct the particulate stream at an angle that is substantially not perpendicular to the plane of the skin.

The direction reduces the total number of collisions between particles as they rain down onto the skin, and thus better preserves their crystalline abrasive properties. The size of the crystalline particle abrasives may be modulated through a process of preparing this for the ideal particle size. Particularly, the average size of the particles may range from 60 microns to 750 microns.

The apparatus further comprises a central control console comprising a housing that comprises a user input means for controlling the delivery of a crystalline abrasive to the skin via the handheld assembly at a velocity sufficient to remove at least some of the epidermis, and for collecting the delivered crystalline abrasive and any skin cells. The user input device may comprise a computer, and/or a touchscreen, and/or a keyboard, humidity controlled chamber and the like. The apparatus may comprise a storage repository (i.e. a hopper) for providing crystalline abrasives to abrade the skin. In some embodiments, the apparatus may further comprise a storage repository for receiving waste material such as crystalline abrasives that have contacted the skin. In some embodiments any such repository is contained within the housing of the apparatus.

Figure 8:
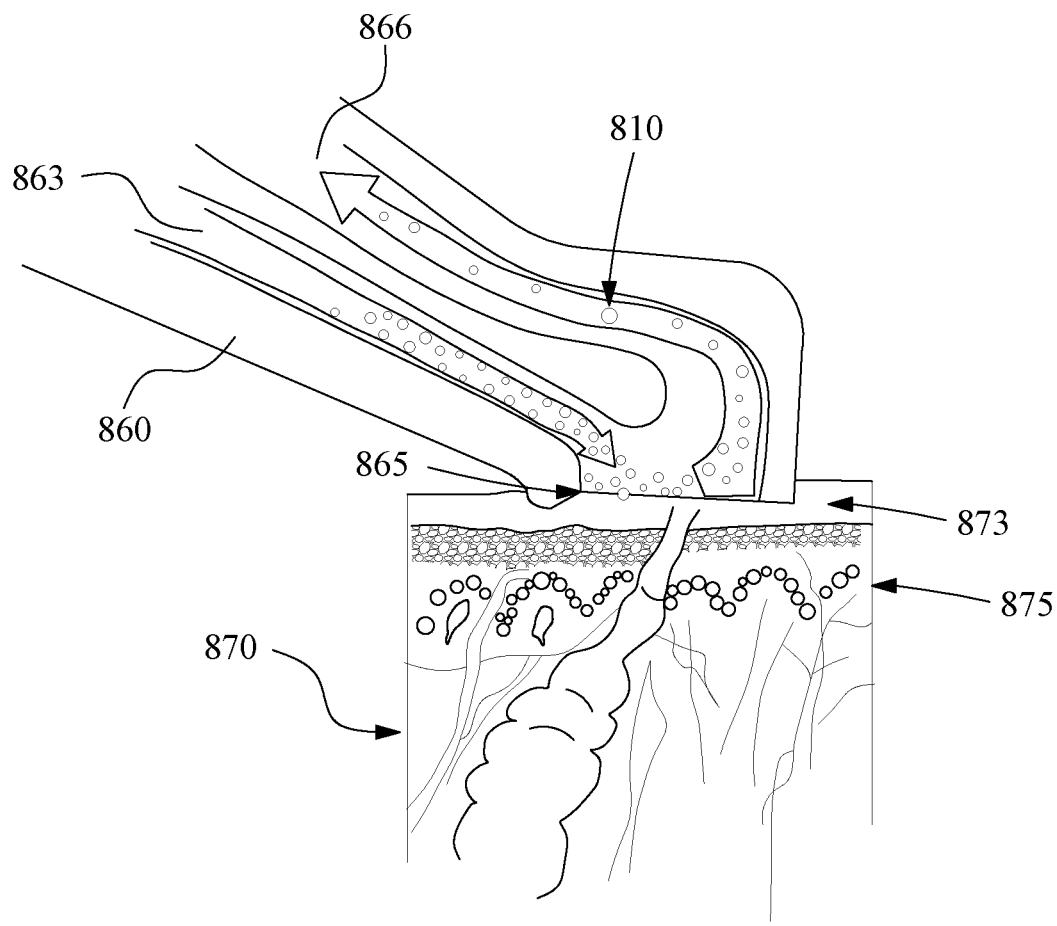

FIG. 8 is a simple graphic illustration 800 of an exemplary handpiece 860 in operation. Salt 810 under positive pressure is input to the subject tissue 870 having upper dermal layer 873 above sub-dermal layer 875. Input channel 863 directs the salt 810 to strike at end portion 865 of the surface interface, which is directed (with exfoliated tissue particles) into output channel 866, having negative pressure to pull the salt/debris away from the treated area.

Treatment in Combination with Ultrasound

Upon completion of the treatment skin using dermal-exfoliation, the skin may be exposed to cosmetically enhancing or therapeutic substances, followed with the use of ultrasound. The use of ultrasound to enhance the delivery and absorption of cosmetically and/or therapeutically enhancing substances is known in the art. Particularly preferred ultrasound frequency ranges of the invention include 1 MHz, 2 MHz, 3 MHz, 3.3 MHz, 5 MHz.

Treatment in Combination with Light-Emitting Devices

Any of the treatments of the present invention may be utilized in combination with light therapy, for example via the adjustable lamp. Light may be provided by any means, with a preference for LED light emission equipment. Regarding the use of light-emitting devices, it is preferred that such devices are selected for spectral power output, rather than total output power. The wavelengths of light may range from 400 nm to 2940 nm, and more preferably from 401 nm to 1550 nm, or most preferably from 404 nm to 950 nm.

Combined treatments of the invention may be focused on treatment of acne. Such treatment may be focused on the range of wavelengths known to kill acne bacteria (404-414 nm) and the wavelength to promote skin repair (660 nm). For anti-aging treatments & for the treatment of stretch marks, red light is used at 660 nm to stimulate skin cell growth and improve collagen networks. Near Infrared light at 930 nm expands capillaries causing better tissue oxygenation and improved access to nutrients, growth factors and the immune system for the treatment of anti-aging treatments and the treatment of stretch marks.

Accordingly, preferred light settings include blue for acne to kill subsurface bacteria that causes pimples. Another preferred light setting includes a combination of red and blue light to treat acne, acne scars, inflammation from acne and pigmentation. Another preferred light setting includes a combination of red and amber (590 nm) for general skin rejuvenation, and particularly to treat superficial reds & browns on the skin. Another preferred light setting includes a combination of red & near infra-red (NIR) for treating pigment and stimulating collagen, skin tightening and for the treatment of stretch marks. Light exposure programs may range from 3-minute exposures to 30-minute program exposures, or any time in between, including, 4, 5, 6, 7, 8, 9, 10, 11, 12, 13, 14, 15, 16, 17, 18, 19, 20, 21, 22, 23, 24, 25, 26, 27, 28 and 29 minute exposures, as well as any secondhand interval there between. Exposure of the skin to the lights may occur in a range from 0.1" to 8.0", including any intervening distance, with a preferable distance being 4.5" from the skin. Such treatment may or may not be combined with other known treatments including antibiotics, retinoic acid, or ACCUTANE™.

Example 1

A typical dermal exfoliation procedure is performed in order to achieve skin rejuvenation, reduction of sun-damage, weather damage and age spots, reduction of irregular pigment patterns in healed scars, smoothing of fine lines, wrinkles and acne pitting, improvement of skin strength, elasticity and smoothness, and for the improvements in the appearance of stretch marks. A typical dermal exfoliation treatment. The protocol will typical be:

- Clean any oil, make-up or other dirt and debris from the area to be treated. Make sure the skin is dry
- Perform the dermal-exfoliation. It is done by keeping the skin taut and pulling the handpiece over the area to be treated. As few as 1 pass across are to be treated and as many as 8 passes across the area to be treated is performed. The treatment can be done in one, two or three different directions (horizontal, vertical and oblique) across the area to be treated.
- Cleanse the treated area of any remaining particle.
- Optionally perform steaming, sonic cleansing and extractions.
- Dermal-exfoliation is used before laser and IPL light therapy, or before micro-needling for the treatment of the appearance of stretch marks, skin rejuvenation, acne, pigmented and red lesions
- Optionally perform the ultrasonic application of topical products to penetrate products such as Vitamin C serums, collagen peptides, glycolic acids, and other antioxidants, and skin rejuvenation topicals, deep into the skin cells
- Optionally use light phototherapy of the invention to help further penetrate and activate topical treatments such as Vitamin C serums, collagen peptides, glycolic acids, other anti-oxidants and skin rejuvenation topicals.

Example 2

The following method is performed order to achieve skin rejuvenation, reduction of sun-damage, weather damage and age spots, reduction of irregular pigment patterns in healed scars, smoothing of fine lines, wrinkles and acne pitting, improvement of skin strength, elasticity and smoothness and for the improvements in the appearance of stretch marks.

Treatment Modalities:

|  | Treatment Period | Red Light (J/cm2) | NIR Light (J/cm2) | Time (Minutes) |
|---|---|---|---|---|
| Skin Rejuvenation | 1× per weekly, 6-12 weeks*8 | 35.8 | 14.4 | 20 |
| Maintenance | 1× monthly | 35.8 | 14.4 | 20 |

*Skin remodeling includes reduction of sun-damage, improvement of skin texture and firmness, reduction of wrinkles, etc. Results usually visible on the third treatment
When dermal-exfoliating, cleanse the treated area of any remaining particle.
Optionally perform the ultrasonic application of topical products to penetrate products such as Vitamin C serums, collagen peptides, glycolic acids, and other anti-oxidant, and skin rejuvenation topicals, deep into the skin cells
Optionally perform steaming, sonic cleansing and extractions.
Use light phototherapy of the invention to help penetrate topical treatments such as Vitamin C serums, or collagen peptides.
Light phototherapy of the invention, used in conjunction with collagen peptides, produces visible improvement in smoothing the appearance of stretch marks, wrinkles and fine lines faster than either phototherapy or collagen treatments alone.
Light phototherapy is a useful after chemical peel treatments to speed the recovery of the skin.

Example 3

This study used a LED device capable of delivering light at a variety of energies including 5 J/cm². A variety of tissue culture and animal model studies were performed to determine the effect of LED light on skin cells. This research study includes tissue culture studies, animal studies and clinical studies with humans. Several wavelengths and intensities were studied in fibroblast (skin cell) tissue culture. In this experimental design, the optimum wavelength for cell proliferation and collagen production was determined to be red light. 660 nm wavelength red light was found to be particularly effective. Animal studies indicated that the edges of wounds were the source of increases in two types of skin cells (fibroblasts and keratinocytes) that were stimulated by the red and near-infrared light. These two cell types then move into the wound area to form new skin. Wound healing in the treated animals was accelerated. Accelerated wound healing was accompanied by increased amounts of tissue growth factors. Studies were performed on soldiers who are required to live for long periods in diving chambers and injured in deep diving conditions. Abrasions, bruising and small cuts under these conditions can become serious due to very slow healing rates. Wound healing with near-infrared light showed improvement to near normal conditions.

Example 4

Promotion of Collagen and Cellular Regeneration

Red & amber light provides an effective skin remodeling treatment useful in anti-aging treatments. Anti-Aging Treatment utilize the following method:

|  | Treatment Period | Red/Amber Light (J/cm2) | Time (Minutes) |
|---|---|---|---|
| Skin Remodeling* | 1-2× weekly, 6-12 weeks** | 12 | 20 |

*Skin remodeling includes reduction of sun-damage, improvement of skin texture and firmness, reduction of wrinkles, and promotes collagen production. Results usually visible on the third treatment.
**Assuming no other active ingredients; red/amber light treatments are used to help penetration and activation of active ingredients such as antioxidants and collagen peptides.

Red & amber light phototherapy is integrated into the current method between the cleanser and the final moisturizing.

1. When dermal-exfoliating, cleanse the treated area of any remaining crystals and follow it with the light phototherapy.
2. Perform steaming, sonic cleansing and extractions first and follow with light phototherapy.
3. Use amber and/or light phototherapy to help penetrate topical treatments such as Vitamin C serums, or collagen peptides.
4. Light phototherapy, in the context of the invention, and used in conjunction with collagen peptides, produces visible improvement in smoothing wrinkles and fine lines faster than either phototherapy or collagen treatments alone.

Example 5

Near Infrared Light to Promote Skin Regeneration: Systemic Effects of Low Intensity Laser Irradiation on Skin Microcirculation in Patients with Diabetic Microangiopathy.

Persons with long-standing diabetes suffer poor circulation in the legs and arms leading to pain, numbness and eventually to neuronal damage and paralysis. A low-level laser device with output comparable to high end LED devices delivering only near-infrared light at 30 J/cm2. Blood flow was measured in the skin area afterwards. Comparisons were made to the blood flow on the other foot or hand which was not illuminated. An improved and sustained blood flow was measured in the illuminated areas that persisted for at least 30 minutes after the illumination was turned off.

The sustained improvement in blood flow in the skin is believed to be due to the near-infrared illumination. It is believed that near infrared light on skin opens the capillaries wider by vasodilation. The near infrared light improves the effect of red light on skin regeneration by improving tissue oxygenation and nutrient access. Near infrared light at this wavelength (930 nm) does not cause tissue heating, or the sensation of heat.

Example 6

Effects of phototherapy on pressure ulcer healing in elderly patients after a falling trauma: A prospective, randomized, controlled study.

The most common treatment for pressure wounds (bedsores) is antibiotics and mechanical manipulation. Typical Stage II wounds take 12-14 weeks to heal. A Stage II pressure wound is serious and poses a threat of severe infection; it is marked by a loss of skin covering and comes before destruction of the underlying tissue. This study used a wand-type LED device delivering red and near-infrared light at up to 5 joules/cm$^2$. Patient wounds were illuminated 3-5 times weekly until the wounds closed. Daily measurements of the wound dimensions were taken. The wounds on these patients healed in 50% of the time compared to untreated wounds.

Example 7

The presently disclosed methods utilizing blue and red light effectively treats mild to very inflamed acne in a period ranging from 0.5 to 3 months, and typically in 1 month. LED in blue mode efficiently activates Amino Levulonic Acid [(ALA)+; (LEVULAN™)] with the optimum wavelength and intensity of blue light. Intense blue light penetrates deep into hair follicles and underneath oil glands where acne colonies remain after benzoyl peroxide treatments. Blue light penetration, approximately 1.5 mm is about four times deeper than most topical treatments are able to penetrate. In addition the effect is highly localized. Blue light creates a toxic event within the bacteria, but is neutral to the skin itself. Topical treatment may be administered prior, including 5% benzoyl peroxide and the oral antibiotic tetracycline. ALA absorbs blue light and becomes activated. This activation is highly toxic to the acne bacteria, but no to surrounding skin cells. The present invention provides the medically proven optimum wavelength and intensity required for this effect.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

I claim:

1. A positive pressure skin exfoliating system, comprising:
    a single air pressure source providing positive pressure;
    a dehumidifier, dehumidifying both air from the air pressure source and air in a chamber comprising a skin exfoliating abrasive container;
    a plurality of dehumidifying stages coupled to the dehumidifier;
    at least one of a controller and a regulator for controlling a pressure value of pressurized air from the air pressure source;
    an input tube with the pressurized and dehumidified air, coupled to the skin exfoliating abrasive container;
    an output tube for collecting waste from a skin treatment site;
    a positive pressure-to-vacuum generating eductor coupled to the output tube; and
    an exfoliating handpiece with an angle of impingement with respect to a subject tissue comprising:
        a hose-end on one side and a skin treatment end on the other side, the hose-end being coupled to the input tube and the output tube;
        a deflection chamber at the skin treatment end;
        a skin interface at a bottom of the deflection chamber; and
        input and output channels traversing an interior of the handpiece from the hose-end to the interior deflection chamber end, the input channel being under a positive pressure from the air pressure source and channeling an abrasive to the skin interface, and the output channel being under a vacuum pressure from the educator and channeling used abrasive and dermal waste from the deflection chamber,
    wherein circulation of abrasive is triggered when the handpiece is in closed contact with the skin.

2. The system of claim 1, wherein the chamber is a sealable chassis.

3. The system of claim 2, wherein the sealable chassis also houses the pressure source, dehumidifying stages, and skin exfoliating abrasive container.

4. The system of claim 1, wherein the container contains a skin exfoliating abrasive that is a salt composed from sodium chloride.

5. The system of claim 1, wherein the container contains a skin exfoliating abrasive that is aluminum oxide or sodium bicarbonate.

6. The system of claim 1, further comprising a waste container connected to at least one of the vacuum eductor and dehumidifying stages.

7. The system of claim 1, wherein the angle of impingement of the handpiece is approximately between 20°-50°, or 15°-45°, or 22°-27°, or approximately 25°.

8. The system of claim 1, further comprising an ultrasonic transducer for treatment of exfoliated skin.

9. The system of claim 8, wherein the ultrasonic transducer operates at a frequency of at least one of 1 MHz, 2 MHz, 3 MHz, 3.3 MHz, or 5 MHz.

10. The system of claim 1, further comprising an adjustable lamp that emits light within a range of 400 nm to 2940 nm.

11. The system of claim 1, wherein the pressurized air is controlled to a maximum of approximately 60 PSI and is provided to ensure the positive pressure is managed and adjusted to a level of between 24-45 PSI.

12. The system of claim 1, wherein the deflection chamber is approximately 13 mm in longitudinal length, and approximately 7 mm in depth.

13. The system of claim 12, wherein the deflection chamber is approximately between 13-16 mm wide and approximately 14 mm tall.

14. The system of claim 1, wherein the angle of impingement of the handpiece is between 22°-27°.

15. The system of claim 1, wherein the handpiece's deflection chamber is longitudinally longer than it is deep.

16. The system of claim 1, wherein the input and output channels travel throughout the length of the handpiece.

17. A method for dermal exfoliation for skin rejuvenation, comprising:
- a single pressuring air source;
- dehumidifying the air; and
- directing an abrasive under positive pressure onto tissue through an angled handpiece, having an angle of impingement of approximately between 20°-50°, or 15°-45°, or 22°-25°, or approximately 25° and having:
    - a hose-end on one side and a skin treatment end on the other side, the hose-end being coupled to an input tube and an output tube;
    - a deflection chamber at the skin treatment end;
    - a skin interface at a bottom of the deflection chamber; and
    - input and output channels traversing an interior of the handpiece from the hose-end to an interior deflection chamber end, the input channel being under a positive pressure from an air pressure source and channeling the abrasive to the skin interface of the handpiece, and the output channel being under an eductor created vacuum pressure and channeling used abrasive and dermal waste from the deflection chamber;
- wherein circulation of the abrasive is triggered when the handpiece is in closed contact with the skin, and wherein at least one of a reduction of sun-damage, weather damage and age spots, reduction of irregular pigment patterns in healed scars, smoothing of fine lines, wrinkles, the treatment of acne and acne pitting, improvement of skin strength, elasticity/smoothness, and appearance of stretch marks is obtained.

18. The method for dermal exfoliation of claim 17, further comprising at applying an ultrasonic signal with a frequency of at least one of 1 MHz, 2 MHz, 3 MHz, 3.3 MHz, or 5 MHz to a treated area.

19. The method for dermal exfoliation of claim 18, further comprising applying a light within a range of 400 nm to 2940 nm to the treated area.

\* \* \* \* \*